(12) United States Patent
Mitchell et al.

(10) Patent No.: US 6,803,107 B2
(45) Date of Patent: Oct. 12, 2004

(54) SURFACE-TREATED SUPERABSORBENT POLYMER PARTICLES

(75) Inventors: Michael A. Mitchell, Waxhaw, NC (US); David Eckert, Palatine, IL (US); Thomas W. Beihoffer, Arlington Heights, IL (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/276,986

(22) PCT Filed: May 17, 2001

(86) PCT No.: PCT/US01/16169

§ 371 (c)(1), (2), (4) Date: May 16, 2003

(87) PCT Pub. No.: WO01/89592

PCT Pub. Date: Nov. 29, 2001

(65) Prior Publication Data

US 2003/0219600 A1 Nov. 27, 2003

Related U.S. Application Data

(63) Continuation-in-part of application No. 09/390,462, filed on Sep. 7, 1999, now Pat. No. 6,239,230.

(51) Int. Cl.⁷ .................................................. B32B 5/16
(52) U.S. Cl. .................... 428/403; 428/407; 525/329.9; 525/374; 525/375; 525/380; 526/306
(58) Field of Search ................................ 428/403, 407; 525/329.9, 375, 374, 386; 526/306

(56) References Cited

U.S. PATENT DOCUMENTS

| | | |
|---|---|---|
| 4,043,952 A | 8/1977 | Ganslaw et al. |
| 4,051,086 A | 9/1977 | Reid |
| 4,076,917 A | 2/1978 | Swift et al. |
| 4,101,606 A | 7/1978 | Cenci et al. |
| 4,115,637 A | 9/1978 | Cenci et al. |
| 4,138,541 A | 2/1979 | Cenci et al. |
| 4,541,871 A | 9/1985 | Obayashi et al. |
| 4,587,308 A | 5/1986 | Makita et al. |
| 4,666,983 A | 5/1987 | Tsubakimoto et al. |
| 4,734,478 A | 3/1988 | Tsubakimoto et al. |
| 4,789,861 A | 12/1988 | Baggett et al. |
| 4,813,945 A | 3/1989 | Le-Khac |
| 4,824,901 A | 4/1989 | Alexander et al. |
| 4,892,533 A | 1/1990 | Le-Khac |
| 5,164,459 A | 11/1992 | Kimura et al. |
| 5,214,101 A | 5/1993 | Pettit, Jr. et al. |
| 5,266,628 A | 11/1993 | Essary et al. |
| 5,384,368 A | 1/1995 | Date et al. |
| 5,409,771 A | 4/1995 | Dahmen et al. |
| 5,669,894 A | 9/1997 | Goldman et al. |
| 5,840,822 A | 11/1998 | Lee et al. |
| 5,858,549 A | 1/1999 | Kielbania, Jr. et al. |
| 6,239,230 B1 * | 5/2001 | Eckert et al. ............ 525/329.9 |

FOREIGN PATENT DOCUMENTS

| | | |
|---|---|---|
| DE | 40 20 780 | 8/1991 |
| EP | 0 509 708 | 10/1992 |
| EP | 0 937 739 A2 | 8/1999 |
| WO | WO 92/16565 | 10/1992 |
| WO | WO 93/05080 | 3/1993 |
| WO | WO 98/06772 | 2/1998 |

OTHER PUBLICATIONS

International Search Report from PCT/US01/16169.
A. Pledger, "Grilesta/Primid™ XL–552 5 years' Successful Market Exposure" publication date unknown.
"Modern Superabsorbent Polymer Technology," Edited by Fredric L. Buchholz et al., pp. 97–109, 1998.
"PRIMID XL–552"—Product Date Sheet (publication date unknown).
Wicks et al., J. Coat. Technol., 57(26), pp. 51–61 (1985).
Stanssens et al., Proc.–Int. Conf. Org. Cot. Scie. Technol., 18th (1992), 435–47, Publisher: Int. Cong. Org. Coag. Sci. Technol., New Paltz, NY.

* cited by examiner

Primary Examiner—Leszek B Kiliman
(74) Attorney, Agent, or Firm—Marshall, Gerstein & Borun LLP

(57) ABSTRACT

Surface-treated superabsorbent polymer particles obtained by mixing 100 parts by weight of superabsorbent polymer particles with 0.001 to 10 parts by weight of a hydroxyalkylamide, and heating the surface-treated superabsorbent polymer particles to crosslink molecular chains existing at least in the vicinity of the surfaces of the superabsorbent polymer particles is disclosed. Surface crosslinking the superabsorbent polymer particles with a hydroxyalkylamide substantially increases both the rate of liquid absorption and the quantity of liquid absorbed and retained by the superabsorbent particles.

39 Claims, No Drawings

SURFACE-TREATED SUPERABSORBENT POLYMER PARTICLES

CROSS-REFERENCE TO RELATED APPLICATIONS

This is a continuation-in-part of U.S. patent application Ser. No. 09/390,462, filed Sep. 7, 1999, now U.S. Pat. No. 6,239,230.

FIELD OF THE INVENTION

The present invention relates to surface-crosslinked superabsorbent polymer particles, and to methods of producing the surface-crosslinked superabsorbent particles. The present invention also relates to the use of the surface-crosslinked particles in articles, such as diapers, catamenial devices, and wound dressings. More particularly, the present invention relates to surface treating superabsorbent polymer (SAP) particles, such as a neutralized, crosslinked, homopolymer or copolymer of acrylic acid, with a hydroxyalkylamide to substantially improve the water absorption and water retention properties of the SAP particles.

BACKGROUND OF THE INVENTION

Water-absorbing resins are widely used in sanitary goods, hygienic goods, wiping cloths, water-retaining agents, dehydrating agents, sludge coagulants, disposable towels and bath mats, disposable door mats, thickening agents, disposable litter mats for pets, condensation-preventing agents, and release control agents for various chemicals. Water-absorbing resins are available in a variety of chemical forms, including substituted and unsubstituted natural and synthetic polymers, such as hydrolysis products of starch acrylonitrile graft polymers, carboxymethylcellulose, crosslinked polyacrylates, sulfonated polystyrenes, hydrolyzed polyacrylamides, polyvinyl alcohols, polyethylene oxides, polyvinylpyrrolidones, and polyacrylonitriles.

Such water-absorbing resins are termed "superabsorbent polymers," or SAPs, and typically are lightly crosslinked hydrophilic polymers. SAPs are generally discussed in Goldman et al. U.S. Pat. Nos. 5,669,894 and 5,599,335, the disclosures of which are incorporated herein by reference. SAPs can differ in their chemical identity, but all SAPs are capable of absorbing and retaining amounts of aqueous fluids equivalent to many times their own weight, even under moderate pressure. For example, SAPs can absorb one hundred times their own weight, or more, of distilled water. The ability to absorb aqueous fluids under a confining pressure is an important requirements for an SAP used in a hygienic article, such as a diaper.

As used here and hereafter, the term "SAP particles" refers to superabsorbent polymer particles in the dry state, i.e., particles containing from no water up to an amount of water less than the weight of the particles. The term "particles" refers to granules, fibers, flakes, spheres, powders, platelets, and other shapes and forms known to persons skilled in the art of superabsorbent polymers. The terms "SAP gel" and "SAP hydrogel" refer to a superabsorbent polymer in the hydrated state, i.e., particles that have absorbed at least their weight in water, and typically several times their weight in water. The terms "surface-treated SAP particle" and "surface-crosslinked SAP particle" refer to an SAP particle having its molecular chains present in the vicinity of the particle surface crosslinked by a compound applied to the surface of the particle. The term "surface crosslinking" means that the level of functional crosslinks in the SAP particle in the vicinity of the surface of the particle is generally higher than the level of functional crosslinks in the SAP particle in the interior of the particle.

SAP particles can differ in ease and cost of manufacture, chemical identity, physical properties, rate of water absorption, and degree of water absorption and retention, thus making the ideal water-absorbent resin a difficult composition to design. For example, the hydrolysis products of starch-acrylonitrile graft polymers have a comparatively high ability to absorb water, but require a cumbersome process for production and have the disadvantages of low heat resistance and decay or decomposition due to the presence of starch. Conversely, other water-absorbent polymers are easily and cheaply manufactured and are not subject to decomposition, but do not absorb liquids as well as the starch-acrylonitrile graft polymers.

Therefore, it would be extremely advantageous to provide a method of increasing the water absorption properties of a stable, easy to manufacture SAP particles to match the superior water absorption properties of a difficult to manufacture particle. Likewise, it would be advantageous to further increase the liquid absorption properties of already superior SAP particles.

In addition, conventional SAP particles all have a serious defect in that their rates of liquid absorption are lower than fluff pulp and paper. For example, when urine is excreted on a disposable diaper containing conventional SAP particles, the urine can remain in contact with the skin for a relatively long time and make the wearer uncomfortable. This is attributed to the low rate at which the diaper can absorb urine.

Attempts have been made to increase the liquid absorption rate by increasing the surface area of the SAP particle, i.e., by decreasing its particle size. However, when the particle size of the SAP particle is decreased, it generally forms a "fish eye" upon contact with urine, which retards the speed of liquid absorption. When the SAP particles are in the form of granules, each granule constitutes a "fish eye" and the speed of liquid absorption decreases. SAP particles in flake form exhibit a moderate increase in the speed of liquid absorption. But, SAP flakes are bulky and are difficult to transport and store.

Initially, the swelling capacity of an SAP particle on contact with liquids, also referred to as free swelling capacity, was the main factor in the design and development of SAP particles. Later, however, it was found that not only is the amount of absorbed liquid important, but the stability of the swollen gel, or gel strength, also important. The free swelling capacity, on one hand, and the gel strength, on the other hand, represent contrary properties. Accordingly, SAP particles having a particularly high absorbency typically exhibit a poor gel strength, such that the gel deforms under pressure (e.g., the load of a body), and prevents further liquid distribution and absorption.

A balanced relation between absorptivity (gel volume) and gel strength is desired to provide proper liquid absorption, liquid transport, and dryness of the diaper and the skin when using SAP particles in a diaper. In this regard, not only is the ability of the SAP particle to retain a liquid under subsequent pressure an important property, but absorption of a liquid against a simultaneously acting pressure, i.e., during liquid absorption also is important. This is the case in practice when a child or adult sits or lies on a sanitary article, or when shear forces are acting on the sanitary article, e.g., leg movements. This absorption property is referred to as absorption under load.

Currently, there is a trend to reduce the size and thickness of sanitary articles for esthetic and environmental reasons (e.g., reduction of waste in landfills). This is accomplished by reducing the large volume of fluff pulp and paper in diapers, and increasing the amount of SAP particles. The SAP particles, therefore, have to perform additional functions with respect to liquid absorption and transport which previously were performed by the fluff pulp and paper, and which could not be accomplished satisfactorily with conventional SAP particles.

Investigators have researched various methods of improving the amount of liquid absorbed and retained by SAP particles, especially under load, and the rate at which the liquid is absorbed. One preferred method of improving the absorption and retention properties of SAP particles is to surface treat the SAP particles.

The surface treatment of SAP particles is well known. For example, U.S. Pat. No. 4,043,952 discloses the use of polyvalent metal compounds as surface treating compounds. U.S. Pat. No. 4,051,086 discloses the use of glyoxal as a surface treatment to improve the absorption rate of SAP particles. The surface treatment of SAP particles with crosslinking agents having two or more functional groups capable of reacting with pendant carboxylate or other groups contained on the polymer comprising the SAP particle is disclosed in various patents. The surface treatment improves absorbency and gel rigidity to improve liquid flowability and prevent SAP particle agglomeration, as well as improving gel strength.

As disclosed in the art, the SAP particles are either mixed with the surface-crosslinking agent optionally using small amounts of water and/or an organic solvent, or an SAP hydrogel containing 10% to 40%, by weight, water is dispersed in a hydrophilic or hydrophobic solvent and mixed with the surface-crosslinking agent.

Prior surface crosslinking agents include diglycidyl ethers, halo epoxy compounds, polyols, polyamines, polyisocyanates, polyfunctional aziridine compounds, and di- or tri-alkylhalides. Regardless of the identity of the surface crosslinking agent, the agent used for the surface treatment has at least two functional groups, and the SAP particles are heated after the surface crosslinking agent is applied to the surface of the SAP particles.

Surface-crosslinked SAP particles, in general, exhibit higher liquid absorption and retention values than SAP particles having a comparable level of internal crosslinks, but lacking surface crosslinking. Internal crosslinks arise from polymerization of the monomers comprising the SAP particles, and are present in the polymer backbone. It has been theorized that surface crosslinking increases the resistance of SAP particles to deformation, thus reducing the degree of contact between surfaces of neighboring SAP particles when the resulting hydrogel is deformed under an external pressure. The degree to which absorption and retention values are enhanced by surface crosslinking is related to the relative amount and distribution of internal and surface crosslinks, and to the particular surface crosslinking agent and method of surface crosslinking.

As understood in the art, surface-crosslinked SAP particles have a higher level of crosslinking in the vicinity of the surface than in the interior. As used herein, "surface" describes the outer-facing boundaries of the particle. For porous SAP particles, exposed internal surface also are included in the definition of surface.

Prior methods of performing surface crosslinking of SAP particles are disclosed, for example, in Obayashi U.S. Pat. No. 4,541,871, WO 92/16565, WO 93/05080, Alexander U.S. Pat. No. 4,824,901, Johnson U.S. Pat. No. 4,789,861, Makita U.S. Pat. No. 4,587,308, Tsubakimoto U.S. Pat. No. 4,734,478, Kimura et al. U.S. Pat. No. 5,164,459, DE 4,020,780, and EPO 509,708. Surface crosslinking of SAPs is generally discussed in F. L. Buchholz et al., ed., "Modern Superabsorbent Polymer Technology," Wiley-VCH, New York, N.Y., pages 97–108 (1998).

A problem encountered in several prior compounds and methods used to surface crosslink SAP particles is the relatively high temperature required to form the surface crosslinks between the SAP and the surface crosslinking agent. Typically, temperatures in excess of 180° C. are required to form the surface crosslinks. At such temperatures, the SAP particle has a tendency to degrade in color from white or off-white to tan or brown. Such color degradation provides an SAP particle that is esthetically unacceptable to consumers. In addition, a high surface crosslinking temperature can increase the residual monomer content of the SAP particle, which can lead to adverse environmental and health effects, or can lead to rejection of the SAP particles for failing to meet specifications.

The present invention is directed to surface-treated SAP particles that overcome the disadvantages associated with prior surface crosslinking agents and with prior surface crosslinked SAP particles.

SUMMARY OF THE INVENTION

The present invention is directed to surface-treated SAP particles and to a method of surface treating SAP particles with a sufficient amount of a hydroxyalkylamide (HAA) to substantially improve the water-absorption and water retention properties of the SAP particles. In particular, the present invention is directed to applying an HAA to a surface of the SAP particle, then heating the surface-treated SAP particles at about 90° C. to about 170° C. for about 60 to about 180 minutes to form surface crosslinks on the SAP particles.

In accordance with the present invention, SAP particles possess improved water absorption and water retention properties as a result surface treatment with a hydroxyalkylamide. Treatment with an HAA is especially effective when performed on polyacrylate salts, hydrolyzed polyacrylamides, or other polymers having a plurality of pendent neutralized carboxyl groups.

Therefore, the present invention is directed to surface-treated SAP particles having about 0.001 to about 10 parts by weight of an HAA per 100 parts by weight of SAP particles, and applied to the surfaces of the SAP particles to crosslink the molecular chains existing at least in the vicinity of the surface of the SAP particles.

One aspect of the present invention is to provide such surface-treated SAP particles, and to a method of manufacturing the surface-treated SAP particles comprising applying a sufficient amount of an HAA to surfaces of the SAP particles and heating the surface-treated SAP particles at a sufficient temperature for a sufficient time for the hydroxyalkylamide to react with pendent groups on a polymer comprising the SAP particle to form surface crosslinks on the SAP particle.

Another aspect of the present invention is to heat the surface-treated SAP particles at about 100° C. to about 160° C. for about 90 to about 150 minutes to form surface crosslinks on the SAP particles.

Yet another aspect of the present invention is to provide surface-treated SAP particles exhibiting a high retention capacity, high gel strength, and high absorbency under load.

This aspect is achieved by surface coating a particle-shaped SAP with about 0.001% to about 10% by weight of a hydroxyalkylamide and subsequently heating to about 90° C. to about 170° C.

Another aspect of the present invention is to provide an SAP particle having surface crosslinks provided by a hydroxyalkylamide having the structure:

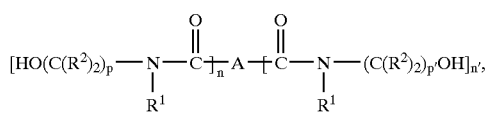

wherein A is a bond, hydrogen, or a monovalent or polyvalent organic radical selected from the group consisting of a saturated or unsaturated alkyl radical containing 1 to 60 carbon atoms, aryl, tri-$C_{1-4}$alkyleneamino, and an unsaturated radical containing one or more ethylenic groups [>C=C<]; $R^1$, selected independently, are hydrogen, straight or branched chain $C_{1-5}$alkyl, or straight or branched chain $C_{1-5}$hydroxyalkyl; $R^2$, selected independently, are radicals selected from the group consisting of hydrogen and straight or branched chain $C_{1-5}$alkyl, or the $R^2$ radicals can be joined to form, together with the carbon atoms, a cycloalkyl ring; p and p', independently, are integers 1 to 4; n is an integer having a value of 1 or 2, and n' is an integer having a value 0 to 2, or when n' is 0, a polymer or copolymer (i.e., n has a value greater than 1, preferably 2 to 10) formed from the hydroxyalkylamide when A is an unsaturated radical.

Another aspect of the present invention is to provide an SAP particle having surface crosslinks provided by a cyclic hydroxyalkylamide having the structure:

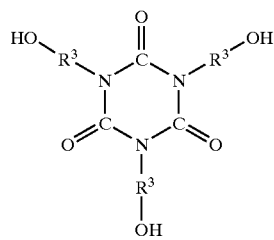

where $R^3$ is a divalent radical selected from the group consisting of an alkylene radical containing 1 to 4 carbon atoms and arylene.

Still another object of the present invention is to provide SAP particles surface crosslinked with a hydroxyalkylamide in an amount sufficient to substantially improve the water absorbency and water retention properties of the SAP particles, such as retention capacity, absorption rate, and gel strength, and to maintain a "dry feel" for the SAP particles after significant liquid absorption.

These and other aspects and advantages of the present invention will become apparent from the following detailed description of the preferred embodiments.

DETAILED DESCRIPTION OF THE PREFERRED EMBODIMENTS

In accordance with the present invention, SAP particles are surface treated with a hydroxyalkylamide to substantially increase the rate of liquid absorption, amount of liquid absorption, and overall retention of liquids by the SAP particles. Surface-treatment of the SAP particles at any time after polymerization and sufficient drying to form solid SAP particles improves liquid absorption properties. For economics and ease of manufacture, the surface treatment is most advantageously performed immediately after the SAP particles are synthesized, dried to an appropriate water content, and sized, such as by grinding.

As will become apparent from the following detailed description of the preferred embodiments, hydroxyalkylamide surface treatment substantially improves the water absorption properties of SAP particles, which can be either acidic or basic in nature. Of particular utility are SAP particles containing a plurality of pendant, neutralized carboxyl groups along the polymer chain.

As stated above, the surface treatment of SAP particles is well known. However, many surface crosslinking agents exhibit disadvantages. Some surface crosslinking agents have toxic properties and, therefore, cannot be used in the sensitive field of hygiene because they pose a threat to health or the environment. For example, in addition to the risk of skin irritation, epoxy, glycidyl, isocyanate, and organic halogen compounds, have a sensitizing effect, and frequently have a carcinogenic and mutagenic potential. Polyamines are avoided as surface crosslinking agents because of possible nitrosamine formation. In any case, when used in diapers and other sanitary articles, residual amounts of toxicologically critical crosslinking agents must be removed from the SAP particles, which involves additional process steps and increases the cost of the SAP particles.

In addition, a majority of the commonly used surface crosslinking agents required heating at temperatures in excess of 180° C. in order to react with the SAP particles and form surface crosslinks. Heating at such a high temperature can increase the residual monomer content of the surface crosslinked SAP particles. An increased residual monomer content poses both toxicological and environmental concerns, and is unacceptable commercially.

The high temperature required to form surface crosslinks also causes the SAP particles to degrade in color from white or off-white to tan or brown. The tan to brown color of the SAP particles is esthetically unacceptable to consumers, who equate the tan to brown color of the SAP particles to an inferior product. The combination of color degradation and increased residual monomer can lead to SAP particles that do not meet production specifications and, therefore, refused by the purchaser and/or consumer. The present invention overcomes these disadvantages associated with prior surface crosslinking agents by utilizing a HAA as the surface crosslinking agent for the SAP particles.

The identity of the SAP particles utilized in the present invention is not limited. The SAP particles are prepared by methods well known in the art, for example, solution or emulsion polymerization. The SAP particles, therefore, can comprise an acidic water-absorbing resin, a basic water-absorbing resin, a blend of an acidic and basic water-absorbing resin, or a multicomponent SAP particle as disclosed in WO 99/25393, the disclosure of which is incorporated herein by reference.

The SAP particles are prepared, for example, by:
(1) copolymerizing an acrylate salt and a crosslinking monomer in aqueous solution, and drying the resulting gel-like hydrous polymer by heating;
(2) dispersing an aqueous solution of acrylic acid and/or an alkali metal acrylate, a water-soluble radical polymerization initiator, and a crosslinkable monomer in an alicyclic and/or an aliphatic hydrocarbon solvent in the presence of a surface-active agent, and subjecting the mixture to suspension polymerization;

(3) saponifying copolymers of vinyl esters and ethylenically unsaturated carboxylic acids or their derivatives;

(4) polymerizing starch and/or cellulose, a monomer having a carboxyl group or capable of forming a carboxyl group upon hydrolysis, and a crosslinking monomer in an aqueous medium, and, as required, hydrolyzing the resulting polymer; or (5) reacting an alkaline substance with a maleic anhydride-type copolymer containing maleic anhydride and at least one monomer selected from α-olefins and vinyl compounds, and, as required, reacting the reaction product with a polyepoxy compound.

Other methods and monomers that provide SAP particles also are known in the art.

Generally, acidic water-absorbing resins have carboxylate, sulfonate, sulfate, and/or phosphate groups incorporated along the polymer chain. Polymers containing these acid moieties are synthesized either from monomers previously substituted with one or more of these acidic functional groups or by incorporating the acidic functional group into the polymer after synthesis. To incorporate carboxyl groups into a polymer, any of a number of ethylenically unsaturated carboxylic acids can be homopolymerized or copolymerized. Carboxyl groups also can be incorporated into the polymer chain indirectly by hydrolyzing a homopolymer or copolymer of monomers such as acrylamide, acrylonitrile, methacrylamide, and alkyl acrylates or methacrylates.

An acidic water-absorbing resin present in an SAP particle can be either a strong or a weak acidic water-absorbing resin. The acidic water-absorbing resin can be a single resin, or a mixture of resins. The acidic resin can be a homopolymer or a copolymer.

The acidic water-absorbing resin typically is a neutralized, lightly crosslinked acrylic-type resin, such as neutralized, lightly crosslinked polyacrylic acid. The lightly crosslinked acidic resin typically is prepared by polymerizing an acidic monomer containing an acyl moiety, e.g., acrylic acid, or a moiety capable of providing an acid group, i.e., acrylonitrile, in the presence of a free radical crosslinker, i.e., a polyfunctional organic compound. The acidic resin can contain other copolymerizable units, i.e., other monoethylenically unsaturated comonomers, well known in the art, as long as the polymer is substantially, i.e., at least 10%, and preferably at least 25%, acidic monomer units. To achieve the full advantage of the present invention, the acidic resin contains at least 50%, and more preferably, at least 75%, and up to 100%, acidic monomer units. The acidic resin is neutralized at least 50 mole %, and preferably at least 70 mole %, with a base prior to surface crosslinking.

Ethylenically unsaturated carboxylic acid and carboxylic acid anhydride monomers, and salts, useful in the acidic water-absorbing resin include acrylic acid, methacrylic acid, ethacrylic acid, α-chloroacrylic acid, α-cyanoacrylic acid, β-methylacrylic acid (crotonic acid), α-phenylacrylic acid, β-acryloxypropionic acid, sorbic acid, α-chlorosorbic acid, angelic acid, cinnamic acid, p-chlorocinnamic acid, β-stearylacrylic acid, itaconic acid, citraconic acid, mesaconic acid, glutaconic acid, aconitic acid, maleic acid, fumaric acid, tricarboxyethylene, 2-methyl-2-butene dicarboxylic acid, maleamic acid, N-phenyl maleamide, maleamide, maleic anhydride, fumaric anhydride, itaconic anhydride, citraconic anhydride, mesaconic anhydride, methyl itaconic anhydride, ethyl maleic anhydride, diethylmaleate, methylmaleate, and maleic anhydride.

Sulfonate-containing acidic resins can be prepared from monomers containing functional groups hydrolyzable to the sulfonic acid form, for example, alkenyl sulfonic acid compounds and sulfoalkylacrylate compounds. Ethylenically unsaturated sulfonic acid monomers include aliphatic or aromatic vinyl sulfonic acids, such as vinylsulfonic acid, allyl sulfonic acid, vinyl toluene sulfonic acid, styrene sulfonic acid, acrylic and methacrylic sulfonic acids, such as sulfoethyl acrylate, sulfoethyl methacrylate, sulfopropyl acrylate, 2-vinyl-4-ethylbenzene, 2-allylbenzene sulfonic acid, 1-phenylethylene sulfonic acid, sulfopropyl methacrylate, 2-hydroxy-3-methacryloxypropyl sulfonic acid, and 2-acrylamide-2-methylpropane sulfonic acid.

Sulfate-containing acidic resins are prepared by reacting homopolymers or copolymers containing hydroxyl groups or residual ethylenic unsaturation with sulfuric acid or sulfur trioxide. Examples of such treated polymers include sulfated polyvinylalcohol, sulfated hydroxyethyl acrylate, and sulfated hydroxypropyl methacrylate. Phosphate-containing acidic resins are prepared by homopolymerizing or copolymerizing ethylenically unsaturated monomers containing a phosphoric acid moiety, such as methacryloxy ethyl phosphate.

Copolymerizable monomers for introduction into the acidic resin, or into the basic resin, include, but are not limited to, ethylene, propylene, isobutylene, $C_1$ to $C_4$ alkyl acrylates and methacrylates, vinyl acetate, methyl vinyl ether, and styrenic compounds having the formula:

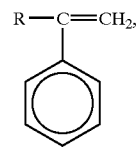

wherein R represents hydrogen or a $C_{1-6}$ alkyl group, and wherein the phenyl ring optionally is substituted with one to four $C_{1-4}$ alkyl or hydroxy groups.

Suitable $C_1$ to $C_4$ alkyl acrylates include, but are not limited to, methyl acrylate, ethyl acrylate, isopropyl acrylate, n-propyl acrylate, n-butyl acrylate, and the like, and mixtures thereof. Suitable $C_1$ to $C_4$ alkyl methacrylates include, but are not limited to, methyl methacrylate, ethyl methacrylate, isopropyl methacrylate, n-propylmethylmethacrylate, -butyl methacrylate, and the like, and mixtures thereof or with $C_{1-4}$ alkyl acrylates. Suitable styrenic compounds include, but are not limited to, styrene, α-methylstyrene, p-methylstyrene, t-butyl styrene, and the like, and mixtures thereof or with $C_{1-4}$ alkyl acrylates and/or methacrylates.

As set forth above, polymerization of acidic monomers, and optional copolymerizable monomers, most commonly is performed by free radical processes in the presence of a polyfunctional organic compound. The acidic resins are crosslinked to a sufficient extent such that the polymer is water insoluble. Crosslinking renders the acidic resins substantially water insoluble, and, in part, serves to determine the absorption capacity of the resins. For use in absorption applications, an acidic resin is lightly crosslinked, i.e., has a crosslinking density of less than about 20%, preferably less than about 10%, and most preferably about 0.01% to about 7%.

A crosslinking agent most preferably is used in an amount of less than about 7 wt %, and typically about 0.1 wt % to about 5 wt %, based on the total weight of monomers. Examples of crosslinking polyvinyl monomers include, but are not limited to, polyacrylic (or polymethacrylic) acid esters represented by the following formula (I); and bisacrylamides, represented by the following formula (II).

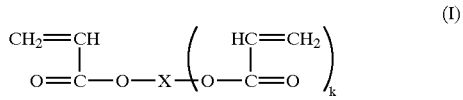

wherein X is ethylene, propylene, trimethylene, cyclohexyl, hexamethylene, 2-hydroxypropylene, —(CH$_2$CH$_2$O)$_p$CH$_2$CH$_2$—, or

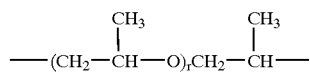

p and r are each an integer 5 to 40, and k is 1 or 2;

wherein 1 is 2 or 3.

The compounds of formula (I) are prepared by reacting polyols, such as ethylene glycol, propylene glycol, trimethylolpropane, 1,6-hexanediol, glycerin, pentaerythritol, polyethylene glycol, or polypropylene glycol, with acrylic acid or methacrylic acid. The compounds of formula (II) are obtained by reacting polyalkylene polyamines, such as diethylenetriamine and triethylenetetramine, with acrylic acid.

Specific crosslinking monomers include, but are not limited to, 1,4-butanediol diacrylate, 1,4-butanediol dimethacrylate, 1,3-butylene glycol diacrylate, 1,3-butylene glycol dimethacrylate, diethylene glycol diacrylate, diethylene glycol dimethacrylate, ethoxylated bisphenol A diacrylate, ethoxylated bisphenol A dimethacrylate, ethylene glycol dimethacrylate, 1,6-hexanediol diacrylate, 1,6-hexanediol dimethacrylate, neopentyl glycol dimethacrylate, polyethylene glycol diacrylate, polyethylene glycol dimethacrylate, triethylene glycol diacrylate, triethylene glycol dimethacrylate, tripropylene glycol diacrylate, tetraethylene glycol diacrylate, tetraethylene glycol dimethacrylate, dipentaerythritol pentaacrylate, pentaerythritol tetraacrylate, pentaerythritol triacrylate, trimethylolpropane triacrylate, trimethylolpropane trimethacrylate, tris(2-hydroxyethyl)isocyanurate triacrylate, tris(2-hydroxyethy)isocyanurate trimethacrylate, divinyl esters of a polycarboxylic acid, diallyl esters or a polycarboxylic acid, triallyl terephthalate, diallyl maleate, diallyl fumarate, hexamethylenebismaleimide, trivinyl trimellitate, divinyl adipate, diallyl succinate, a divinyl ether of ethylene glycol, cyclopentadiene diacrylate, tetraallyl ammonium halides, or mixtures thereof. Compounds such as divinylbenzene and divinyl ether also can be used to crosslink the poly(dialkylaminoalkyl acrylamides). Especially preferred crosslinking agents are N,N'-methylenebisacrylamide, N,N'-methylenebismethacrylamide, ethylene glycol dimethacrylate, and trimethylolpropane triacrylate.

The acidic resin, either strongly acidic or weakly acidic, can be any resin that acts as an SAP in its neutralized form. Examples of acidic resins include, but are not limited to, polyacrylic acid, hydrolyzed starch-acrylonitrile graft copolymers, starch-acrylic acid graft copolymers, saponified vinyl acetate-acrylic ester copolymers, hydrolyzed acrylonitrile copolymers, hydrolyzed acrylamide copolymers, ethylene-maleic anhydride copolymers, isobutylene-maleic anhydride copolymers, poly(vinylsulfonic acid), poly(vinylphosphonic acid), poly(vinylphosphoric acid), poly(vinylsulfuric acid), sulfonated polystyrene, poly(aspartic acid), poly(lactic acid), and mixtures thereof. The preferred acidic resins are the polyacrylic acids.

The final acidic SAP particle contains from about 50 to 100 percent neutralized pendant carboxylate salt units. Accordingly, it may be necessary to neutralize carboxylic acid groups. Neutralization of carboxylic acid groups is accomplished using a strong organic or inorganic base, such as sodium hydroxide, potassium hydroxide, ammonia, ammonium hydroxide, or an organic amine.

The sequence and the number of reactions (e.g., polymerization, hydrolysis, and neutralization) performed to obtain the desired acid functionality attached to acidic resin backbone are not critical. Any number and sequence resulting in a final SAP particle which possesses 0 to about 90 percent copolymerizable monomer units and about 10 to about 100 percent monomer units having pendant acid groups, and neutralized at least 50 mole %, is suitable.

Analogous to the acidic resin, a basic water-absorbing resin present in the SAP particles can be a strong or weak basic water-absorbing resins. The basic water-absorbing resin can be a single resin or a mixture of resins. The basic resin can be a homopolymer or a copolymer. The identity of the basic resin is not limited as long as the basic resin is capable of reacting with a β-HAA. The strong basic resins typically are present in the hydroxide (OH) or bicarbonate (HCO$_3$) form.

The basic water-absorbing resin typically is a lightly crosslinked acrylic-type resin, such as a poly(vinylamine). The basic resin also can be a polymer such as a lightly crosslinked polyethylenimine, a poly(allylamine), a poly(allylguanidine), a poly(dimethyldiallylammonium hydroxide), a quaternized polystyrene derivative, such as

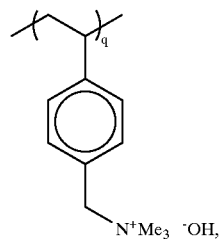

a guanidine-modified polystyrene, such as

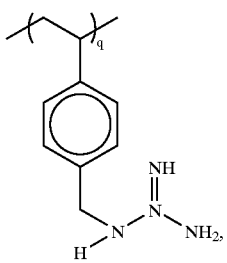

a quaternized poly((meth)acrylamide) or ester analog, such as

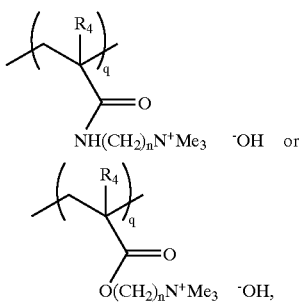

wherein Me is methyl, $R_4$ is hydrogen or methyl, n is a number 1 to 8, and q is a number from 10 to about 100,000, or a poly(vinylguanidine), i.e., poly(VG), a strong basic water-absorbing resin having the general structural formula (III)

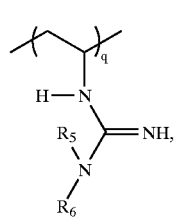

(III)

wherein q is a number from 10 to about 100,000, and $R_5$ and $R_6$, independently, are selected from the group consisting of hydrogen, $C_1$–$C_4$ alkyl, $C_3$–$C_6$ cycloalkyl, benzyl, phenyl, alkyl-substituted phenyl, naphthyl, and similar aliphatic and aromatic groups. The lightly crosslinked basic water-absorbing resin can contain other copolymerizable units and is crosslinked using a polyfunctional organic compound, as set forth above with respect to the acidic water-absorbing resin.

A basic water-absorbing resin used in the present SAP particles typically contains an amino or a guanidine group. Accordingly, a water-soluble basic resin can be crosslinked in solution by suspending or dissolving an uncrosslinked basic resin in an aqueous or alcoholic medium, then adding a di- or polyfunctional compound capable of crosslinking the basic resin by reaction with the amino groups of the basic resin. Such crosslinking agents include, for example, multifunctional aldehydes (e.g., glutaraldehyde), multifunctional acrylates (e.g., butanediol diacrylate, TMPTA), halohydrins (e.g., epichlorohydrin), dihalides (e.g., dibromopropane), disulfonate esters (e.g., $ZS(O_2)O$—$(CH_2)_n$—$OF(O)_2Z$, wherein n is 1 to 10, and Z is methyl or tosyl), multifunctional epoxies (e.g., ethylene glycol diglycidyl ether), multifunctional esters (e.g., dimethyl adipate), multifunctional acid halides (e.g., oxalyl chloride), multifunctional carboxylic acids (e.g., succinic acid), carboxylic acid anhydrides (e.g., succinic anhydride), organic titanates (e.g., TYZOR A A from DuPont), melamine resins (e.g., CYMEL 301, CYMEL 303, CYMEL 370, and CYMEL 373 from Cytec Industries, Wayne, N.J.), hydroxymethyl ureas (e.g., N,N'-dihydroxymethyl-4,5-dihydroxyethylene-urea), and multifunctional isocyanates (e.g., toluene diisocyanate or methylene diisocyanate). Crosslinking agents for basic resins also are disclosed in Pinschmidt, Jr. et al. U.S. Pat. No. 5,085,787, incorporated herein by reference, and in EP 450 923.

Conventionally, the crosslinking agent is water or alcohol soluble, and possesses sufficient reactivity with the basic resin such that crosslinking occurs in a controlled fashion, preferably at a temperature of about 25° C. to about 150° C. Preferred crosslinking agents are ethylene glycol diglycidyl ether (EGDGE), a water-soluble diglycidyl ether, and a dibromoalkane, an alcohol-soluble compound.

The basic resin, either strongly or weakly basic, therefore, can be any resin that acts as an SAP in its charged form. Examples of basic resins include a poly(vinylamine), a polyethylenimine, a poly(vinylguanidine), a poly(allylamine), a poly(allylguanidine), or a poly(dialkylaminoalkyl (meth)acrylamide) prepared by polymerizing and lightly crosslinking a monomer having the structure

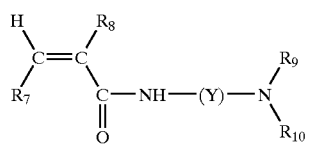

or its ester analog

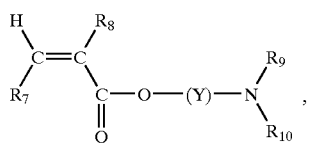

wherein $R_7$ and $R_8$, independently, are selected from the group consisting of hydrogen and methyl, Y is a divalent straight chain or branched organic radical having 1 to 8 carbon atoms, $R_9$ is hydrogen, and $R_{10}$ is hydrogen or an alkyl radical having 1 to 4 carbon atoms. Preferred basic resins include a poly(vinylamine), polyethylenimine, poly(vinylguanadine), poly(methylaminoethyl acrylamide), and poly(methylaminopropyl methacrylamide).

There is no particular restriction on the shape of the SAP particles used in this invention. The SAP particles can be in the form of spheres obtained by inverse phase suspension polymerization, flakes obtained by drum drying, or irregularly shaped particles obtained by pulverizing solid polymer. From the standpoint of the speed of absorption, the SAP particles preferably are small, and typically the particle size is about 20 to about 2000 μm, preferably about 50 about 850 μm.

The SAP particles, comprising an acidic resin, basic resin, a blend of acidic and basic resin, or multicomponent SAP particles, are surface treated by applying a surface crosslinking agent to the surface of the SAP particles, followed by heating the particles. Surface treatment results in surface crosslinking of the SAP particles. It has been found that surface treating SAP particles with a β-hydroxyalkylamide enhances the ability of the SAP particles to absorb and retain aqueous media under a load.

In general, surface crosslinking is achieved by contacting SAP particles with a solution of an HAA to wet predominantly only the outer surfaces of the SAP particles. Surface crosslinking of the SAP particles then is performed, preferably by heating at least the wetted surfaces of the SAP particles.

The surface crosslinking agent utilized in the present invention is a hydroxyalkylamine. For example, HAAs are disclosed in Swift et al. U.S. Pat. No. 4,076,917, incorporated herein by reference. An HAA useful in the present invention has the following formula:

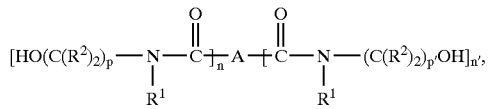

wherein A is a bond, hydrogen, or a monovalent polyvalent organic radical selected from the group consisting of a saturated or unsaturated alkyl radical contain 1 to 60 carbon atoms, such as methyl, ethyl, propyl, butyl, pentyl, hexyl, heptyl, octyl, nonyl, decyl, eicosyl, triacontyl, tetracontyl, pentacontyl, hexylcontyl, and the like, aryl, for example, mono- and dicyclic aryl, such as phenyl, naphthyl, and the like, tri-$C_{1-4}$ alkyleneamine, such as trimethyleneamino, triethyleneamino, and the like, and an unsaturated radical containing one or more ethylenic groups [>C=C<], such as ethenyl, 1-methylethenyl, 3-butenyl-1,3-diyl, 2-propenyl-1, 2-diyl, carboxy $C_{1-4}$ alkenyl, such as 3-carboxy-2-propenyl, and the like, $C_{1-4}$ alkoxy carbonyl lower alkenyl, such as 3-methoxycarbonyl-2-propenyl, and the like; $R^1$, selected independently, are hydrogen, straight or branched chain $C_{1-5}$ alkyl, such as methyl, ethyl, n-propyl, n-butyl, sec-butyl, tert-butyl, pentyl, and the like, or straight or branched chain $C_{1-5}$ hydroxyalkyl, such as hydroxyethyl, 3-hydroxypropyl, 2-hydroxypropyl, 4-hydroxybutyl, 3-hydroxybutyl, 2-hydroxy-2-methylpropyl, 5-hydroxypentyl, 4-hydroxypentyl, 3-hydroxypentyl, 2-hydroxypentyl, and the isomers of pentyl; $R^2$, selected independently, are radicals selected from the group consisting of hydrogen and straight or branched $C_{1-5}$ alkyl, or the $R^2$ radicals can be joined to form, together with the carbon atoms, a cycloalkyl ring, such as cyclopentyl, cyclohexyl, and the like; p and p', independently, are an integer 1 to 4; n is an integer having a value of 1 or 2, and n' is an integer having a value of 0 to 2, or when n' is 0, a polymer or copolymer (i.e., n has a value greater than 1, preferably 2–10) formed from the β-hydroxyalkylamide when A is an unsaturated radical.

Preferred HAAs are wherein $R^1$ is H or $C_{1-5}$hydroxyalkyl, n and n' are each 1, —A— is —$(CH_2)_m$—, m is 0–8, preferably 2–8, each $R^2$ on the α-carbon is H, and one of the $R^2$ radicals on the beta carbon in each case is H and the other is H or a $C_{1-5}$ alkyl, and q and q', independently, are an integer 1 to 3; that is,

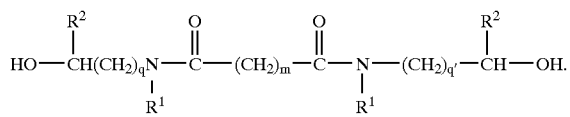

Most preferred HAAs have the formula:

wherein both $R^2$ groups are H or both $R^2$ groups are —$CH_3$.

Specific examples of HAA compounds include, but are not limited to, bis[N,N-di(β-hydroxyethyl)]adipamide, bis[N,N-di(β-hydroxypropyl)]succinamide, bis[N,N-di(β-hydroxyethyl)]azelamide, bis[N-N-di(β-hydroxypropyl)] adipamide, and bis[N-methyl-N-(β-hydroxyethyl)]oxamide. A commercially available β-HAA is PRIMID™ XL-552 from EMS-CHEMIE, Dornat, Switzerland. PRIMID™ XL-522 has the structure

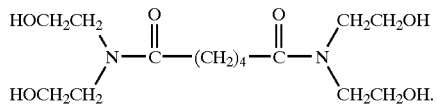

Another commercially available HAA is PRIMID™ QM-1260 from EMS-CHEMIE, having the structure:

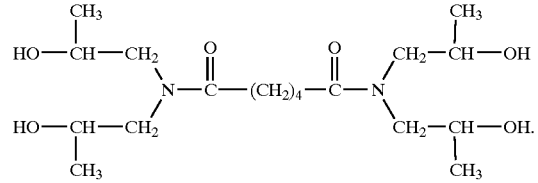

In another embodiment, the HAA has the cyclic structure

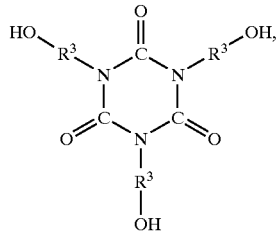

wherein $R^3$ is a divalent radical selected from the group consisting of an alkylene radical containing 1 to 4 carbon atoms and arylene. In preferred embodiments, $R^3$, independently, is $(CH_2)_2$, $(CH_2)_3$, or

Additional HAA compounds are the N-substituted ethylhydroxy, methyl and ethylhydroxy, and di(ethylhydroxy) derivatives of oxamide, malonamide, succinamide, glutaramide, adipamide, maleamide, a mixture of succinamide and glutaramide, and —(C=O)$CH_2$O$CH_2$C(=O)—. Such compounds include, but are not limited to, bis[N-methyl-N-(β-hydroxyethyl)]succinamide, bis[N-methyl-N-(β-hydroxyethyl)]glutaramide, bis[N-methyl-N-(β-hydroxyethyl)]succinamide/glutaramide, bis[N,N-(dihydroxyethyl)]succinamide, bis[N,N-(dihydroxyethyl)]glutaramide, bis[N,N-(dihydroxyethyl)]succinamide/glutaramide, bis[N,N-(dihydroxyethyl)]succinamide/glutaramide/adipamide, bis[N,N-(dihydroxyethyl)]glutaramide/adipamide, and other mixtures and similar compounds.

Typically, the SAP particles are surface treated using a solution of an HAA. The solution contains about 0.01% to about 4%, by weight, HAA, and preferably about 0.4% to about 2%, by weight, HAA in a suitable solvent, for example, water, an alcohol, or a glycol. The solution can be applied as a fine spray onto the surface of freely tumbling SAP particles at a ratio of about 1:0.01 to about 1:0.5 parts by weight SAP particles to solution of HAA.

To achieve the desired absorption properties, the HAA is distributed evenly on the surfaces of the SAP particles. For this purpose, mixing is performed in suitable mixers, e.g., fluidized bed mixers, paddle mixers, a rotating disc mixer, a ribbon mixer, a screw mixer, milling rolls, or twin-worm mixers.

The amount of HAA used to surface treat the SAP particles varies depending upon the identity of SAP particles. Generally, the amount of HAA used to surface treat the SAP particles in about 0.001 to about 10 parts by weight per 100 parts by weight of the SAP particles. When the amount of HAA exceeds 10 parts by weight, the SAP particles are too highly surface crosslinked, and the resulting SAP particles have a reduced absorption capacity. On the other hand, when SAP particles are surface crosslinked with less than 0.001 part by weight HAA, there is no observable effect.

A preferred amount of HAA used to surface crosslink the SAP particles is about 0.01 to about 5 parts by weight per 100 parts, by weight, SAP particles. To achieve the full advantage of the present invention, the amount of HAA used as a surface crosslinking agent is about 0.05 to about 1 part, by weight, per 100 weight parts of SAP particles.

The drying and surface crosslinking of the surface-treated SAP particles are achieved by heating the surface-treated particles at a suitable temperature, e.g., about 90° C. to about 170° C., and preferably about 100° C. to about 165° C. To achieve the full advantage of the present invention, the surface-treated particles are heated at about 100° C. to about 160° C. At this temperature, the SAP particles are surface crosslinked with the HAA without degrading the color of the SAP particles and without increasing the residual monomer content of the SAP particles.

The surface-treated SAP particles are heated for about 60 to about 180 minutes, preferably about 60 to about 150 minutes, to effect surface crosslinking. To achieve the full advantage of the present invention, the SAP particles are heated for about 75 to about 120 minutes.

Ordinary dryers or heating ovens can be used for heating the surface-treated SAP particles and the HAA. Such heating apparatus includes, for example, an agitated trough dryer, a rotating dryer, a rotating disc dryer, a kneading dryer, a fluidized bed dryer, a pneumatic conveying dryer, and an infrared dryer. However, any other method of reacting the HAA with the polymer of the SAP particle to achieve surface crosslinking of the SAP particles, such as microwave energy, can be used. In the surface treating and surface crosslinking steps, the mixer can be used to perform simultaneous mixing and heating of the HAA and SAP particles, if the mixer is of a type that can be heated.

As previously stated, surface treating with an HAA, and subsequent or simultaneous heating, provides additional polymer crosslinks in the vicinity of the surface of the SAP particles. The gradation in crosslinking from the surface of the SAP particles to interior, i.e., the anisotropy of crosslink density, can vary, both in depth and profile. Thus, for example, the depth of surface crosslinking can be shallow, with a relatively sharp transition from a high level to a low level of crosslinking. Alternatively, for example, the depth of surface crosslinking can be a significant fraction of the dimensions of the SAP particle, with a broader transition.

Depending on size, shape, porosity, as well as functional considerations, the degree and gradient of surface crosslinking can vary within a given type of SAP particle. Depending on variations in surface:volume ratio within the SAP particles (e.g., between small and large particles), it is typical for the overall level of crosslinking to vary over the group of SAP particles (e.g., is greater for smaller particles).

Surface crosslinking generally is performed after the final boundaries of the SAP particles are essentially established (e.g., by grinding, extruding, or foaming). However, it is also possible to effect surface crosslinking concurrently with the creation of final boundaries. Furthermore, some additional changes in SAP particle boundaries can occur even after surface crosslinks are introduced.

The following examples illustrate the present surface crosslinked SAP particles. It should be understood, however, that these examples are merely illustrative, and that the scope of this invention is not limited to these examples.

In the following examples, the SAP particles are lightly crosslinked polyacrylic acid polymers, neutralized about 75% to about 80% with sodium hydroxide. The sodium polyacrylate was made by methods well known in the art.

EXAMPLE 1

A 2% to 50%, by weight, solution of PRIMID™ XL-552 in water was applied to the surface of the SAP particles, at the rate of 3 to 7 grams of the HAA solution per 100 grams of SAP particles. The surface-treated SAP particles then were heat treated at about 150° C. to about 170° C. for about 60 to about 150 minutes. The best results were achieved using a greater than 10% PRIMID™ XL-552 solution applied at about 7 grams of HAA solution per 100 grams of SAP particles, then heat treating for 135 to 150 minutes at about 165° C. The performance results are summarized in Table 1.

EXAMPLE 2

A solution containing 1% to 5%, by weight, of PRIMID™ XL-552 and 0% to 37.5%, by weight, propylene glycol in water was applied to the surface of SAP particles, at the rate of about 4 to about 10 grams of solution per 100 grams of SAP particles. The surface-treated SAP particles then were heat treated at about 150° C. to about 170° C. for about 60 to about 120 minutes. The best results were achieved using a 3.5% PRIMID™ XL-552/25% propylene glycol solution applied at about 7 grams of solution per 100 grams of SAP particles, then heat treating for about 120 minutes at 160° C. The performance results are summarized in Table 1.

EXAMPLE 3

A solution containing 1% to 5%, by weight, PRIMID™ XL-552 and 0% to 25%, by weight, 1,3-butanediol in water was applied to the surface of SAP particles, at the rate of about 4 to about 10 grams of solution per 100 grams of SAP particles. The surface-treated SAP particles then were heat treated at about 150° C. to about 170° C. for about 60 to about 120 minutes. The best results were achieved using a 3.5% PRIMID™ XL-552/25% 1,3-butanediol solution applied at about 7 grams of solution per 100 grams of SAP particles, then heat treating for about 120 minutes at about 160° C. The performance results are summarized in Table 1.

EXAMPLE 4

A solution containing 1% to 5%, by weight, PRIMID™ XL-552 and 0 to 25% 1,4-butanediol in water was applied to the surface of SAP particles, at the rate of about 4 to about 10 grams of solution per 100 grams of SAP particles. The surface-treated SAP particles then were heat treated at about 150° C. to about 170° C. for about 60 to about 120 minutes. The best results were achieved using a 3.5% PRIMID™ XL-552/25% 1,4-butanediol solution applied at about 7 grams of solution per 100 grams of SAP particles, then heat treating for about 120 minutes at 160° C. The performance results are summarized in Table 1.

EXAMPLE 5

A solution containing 1% to 5%, by weight, PRIMID™ XL-552 and 0% to 25%, by weight, ethanol in water was applied to the surface of SAP particles, at the rate of about 4 to about 10 grams of solution per 100 grams of SAP particles. The surface-treated SAP particles then were heat treated at 150° C. to about 170° C. for about 60 to about 120 minutes. The best results were achieved using a 3.5% PRIMID™ XL-552/25% ethanol solution applied at about 7 grams of solution per 100 grams of polymer, then heat treating for about 120 minutes at 160° C. The performance results are summarized in Table 1.

Examples 1–5 illustrate that the scope of cosolvents (e.g., ethanol) and additional surface crosslinking agents (e.g., a diol) that can be used in combination with the HAA is broad. Examples of cosolvents include, but are not limited to, alcohols, e.g., methanol, ethanol, and isopropanol, and ketones, e.g., acetone.

An additional surface crosslinking agent can be any compound that reacts with a pendant moiety of the polymer comprising the SAP particles, and that inhibits the swell of SAP particles, can be used in conjunction with the HAA. Examples of additional surface crosslinking agents include, but are not limited to, diols, triols, polyols, e.g., ethylene glycol, propylene glycol, and 1,3-butanediol, and similar hydroxyl-containing compounds. Divalent and trivalent metal salts can be used as additional surface crosslinking agents, as swell suppressants. The HAA also can be used in combination with other surface crosslinking agents, such as EGDGE, and especially with any other surface crosslinking compound that can react with the polymer comprising the SAP particles at temperatures below 160° C.

The following Table 1 summarizes various specific surface crosslinked SAP particles generally disclosed in Examples 1–5, and the adsorbent properties exhibited by the surface crosslinked SAP particles. In the test results set forth in Table 1, the surface-treated SAP particles were tested for absorption under load at 0.7 psi (AUL (0.7 psi)). Absorption under load (AUL) is a measure of the ability of an SAP to absorb fluid under an applied pressure. The AUL was determined by the following method as disclosed in U.S. Pat. No. 5,149,335, incorporated herein by reference.

An SAP (0.160 g+/−0.001 g) is carefully scattered onto a 140-micron, water-permeable mesh attached to the base of a hollow Plexiglas cylinder with an internal diameter of 25 mm. The sample is covered with a 100 g cover plate and the cylinder assembly weighed. This gives an applied pressure of 20 g/cm² (0.28 psi). Alternatively, the sample can be covered with a 250 g cover plate to give an applied pressure of 51 g/cm² (0.7 psi). The screened base of the cylinder is placed in a 100 mm petri dish containing 25 milliliters of a test solution (usually 0.9% saline), and the polymer is allowed to absorb for 1 hour (or 3 hours). By reweighing the cylinder assembly, the AUL (at a given pressure) is calculated by dividing the weight of liquid absorbed by the dry weight of polymer before liquid contact.

The test results in Table 1 also set forth the centrifuge retention capacity (CRC) of the test samples. The centrifuge retention capacity of an SAP is a measure of the absorptive capacity of the SAP. In particular, the CRC test is a method of determining the absorbent capacity of an SAP in grams of 0.9% saline (NaCl) solution per gram of polymer. This test includes swelling the SAP in a "teabag" immersed in 0.9% NaCl solution for 30 minutes, then centrifuged for three minutes. The ratio of retained liquid weight to initial weight of the dry SAP is the absorptive capacity of the superabsorbent polymer, or the CRC.

The CRC test was performed as follows:

Apparatus
  Electronic Balance, accuracy of 0.0001 gram
  Plastic Tray, 44 cm×39 cm×10 cm
  Heat sealer, T-bar plastic model
  Teabag material (CH DEXTER), cut and sealed to produce a teabag 6.25×8.5 cm
  Weigh paper or plastic weighing boat
  Timer
  Centrifuge capable of 1400 rpm, 230 mm diameter
  Tongs
Materials
  SAP test sample
  0.9% NaCl solution prepared with distilled or deionized water
Sample Preparation
  (10 Samples Per Set Maximum 20 Samples Per 2000 ml NaCl Solution)
  a) Pour approximately 2000 ml of NaCl solution into the tray. The liquid filling height should be approximately ½ inch.
  b) Fold teabag paper and seal two sides with heat sealer, leaving one side open for polymer addition. Samples may be run in duplicate (optional).
  c) Weight 0.2000+/−0.0050 grams polymer onto weigh paper or plastic weighing boat. Record weight and number.
  d) Mark teabag with corresponding sample number. Transfer polymer to teabag and close open end with heat sealer.
  e) Seal an empty teabag and mark it "blank."
  f) Set the timer for 30 minutes. Hold each teabag horizontally and distribute the polymer evenly throughout the bag. Lay filled teabags and the blank on the surface of the NaCl solution. Submerge each teabag using a spatula to allow complete wetting. Start the timer.
  Filled teabags were handled carefully with tongs, contacting only the edge of the teabag and not the area filled with polymer.
Centrifuge
  a) After 20 minutes soak time, remove filled teabags and blank from NaCl solution. Position the teabags in the centrifuge with each bag sticking to the outer wall of the centrifuge basket.
  b) Close the centrifuge lid. Set the timer for 3 minutes. Start the centrifuge (ramp up quickly to 1400 rpm) and the timer at the same time. After 3 minutes, turn off the centrifuge (and apply the brake if necessary).
  c) Weigh each filled teabag and blanks. Record weights.
Calculation $$CFC\ (g/g) = \frac{\text{final weight of teabag} - \text{final weight of blank} - \text{dry polymer weight}}{\text{dry polymer weight}}.$$

TABLE 1

| Sample | Coating[1] | CR[3] | Temp.[4] | Time[5] | CRC[6] | 0.7 AUL |
|---|---|---|---|---|---|---|
| 1 | 10% XL-552[2] Soln[8] | 0.07 | 165° C. | 150 min. | 32.4 | 20.2 |
| 2 | 25% XL-552 Soln | 0.07 | 165° C. | 135 min. | 29.5 | 23.3 |

TABLE 1-continued

| Sample | Coating[1] | CR[3] | Temp.[4] | Time[5] | CRC[6] | 0.7 AUL |
|---|---|---|---|---|---|---|
| 3 | 37.5% XL-552 Soln | 0.07 | 165° C. | 135 min. | 30.7 | 22.8 |
| 4 | 50% XL-552 Soln | 0.07 | 165° C. | 135 min. | 30.4 | 22.1 |
| 5 | 5% XL-552/25% Ethanol | 0.07 | 165° C. | 150 min. | 31.5 | 26.2 |
| 6 | 3.5% XL-552/25% Propylene Glycol | 0.07 | 160° C. | 120 min. | 28.5 | 25.4 |
| 7 | 3.5% XL-552/25% 1,3-Butanediol | 0.07 | 160° C. | 120 min. | 31.2 | 26.4 |
| 8 | 3.5% XL-552/25% 1,4-Butanediol | 0.07 | 160° C. | 120 min. | 28 | 26.3 |
| 9[7] | 25% Propylene Glycol Only | 0.07 | 160° C. | 120 min. | 33.0 | 10.4 |
| 10[7] | 25% 1,3-Butanediol Only | 0.07 | 160° C. | 120 min. | 33.6 | 10.4 |
| 11[7] | 25% 1,4-Butanediol Only | 0.07 | 160° C. | 120 min. | 32.4 | 11.8 |

[1]Surface crosslinking composition;
[2]XL-552 is PRIMID ™ XL-552;
[3]CR is a ratio of surface crosslinking composition applied to the surface of the SAP particles, based on SAP weight;
[4]Heating temperature;
[5]Heating time;
[6]CRC is retention capacity, in g 0.9% NaCl per g of dry SAP;
[7]Samples 9–11 are comparative examples; and
[8]All Samples 1–11 contain sufficient water to attain 100% solution weight.

The data in Table 1 shows that surface crosslinking using an HAA provides surface-treated SAP particles having a greatly improved AUL (Samples 1–8) compared to SAP particles surface crosslinked only with a diol (Samples 9–11). In addition, an HAA surface crosslinker increased the AUL, without adversely affecting the CRC, which is both beneficial and unexpected in the art.

In another test, SAP particles were surface crosslinked with PRIMID™ QM-1260. The results of this test, and the conditions used in the crosslinking reaction and in the tests, are set forth in Table 2. The SAP sample crosslinked with PRIMID™ QM-1260 (i.e., Sample 13) was compared to an SAP sample crosslinked with an equal amount of PRIMID™ XL-552 (Sample 12). Table 2 illustrates that an SAP crosslinking with PRIMID™ QM-1260 provides improved absorption properties (compare Sample 13 to control Samples 9–11).

TABLE 2

| Sample # | Coating[1] | CR[3] | Temp[4] | Time[5] | CRC[6] | 0.7 AUL |
|---|---|---|---|---|---|---|
| 12 | 4.9% wt XL-552, 25% propylene glycol | 0.06 | 160 | 120 min | 28.5[10] | 23.8 |

TABLE 2-continued

| Sample # | Coating[1] | CR[3] | Temp[4] | Time[5] | CRC[6] | 0.7 AUL |
|---|---|---|---|---|---|---|
| 13 | 4.9% wt QM-1260[9], 25% propylene glycol | 0.06 | 160 | 120 min | 32.4 | 16.5 |

[9]QM-1260 is PRIMID ™ QM-1260; and
[10]CRC of control SAP particles lacking surface crosslinks is 34.3.

The following Table 3 illustrates additional Examples 14–39 of SAP particles surface crosslinked with various HAA compounds. The HAA compounds listed in Table 3 have the following general structural formula L—A—L. The individual L and A portions of the HAA compounds are defined in Table 3.

The HAA compounds of Examples 14–39 were prepared by admixing a starting amine (e.g., diethanolamine) and a dimethyl ester of a dicarboxylic acid. No solvent is required, but can be added to the reaction mixture if desired. The starting materials are liquids, therefore, the mixing step is rapid. Optionally, catalytic amount of sodium hydroxide or potassium hydroxide can be added to the reaction mixture. The reaction mixture then is heated to the reaction temperature (e.g., 120° C.). Methanol distills from the reaction mixture and is condensed. The reaction time at this temperature is about 4 hours, and the reaction is essentially quantitative. The resulting HAA typically is a viscous amber liquid, but some HAAs can crystallize. A solvent, e.g., water or propylene glycol, can be added to the reaction mixture prior to cooling to lower viscosity and prevent compound crystallization. No purification step is needed in the synthesis of an HAA.

In particular, the HAA compounds in the following table were prepared using the following procedure. One molar equivalent of a carboxylic acid diester and 1.24 mol % potassium hydroxide were added to a flask, and the resulting mixture was stirred for 5 minutes under an argon blanket. A water aspirator was used to pull a vacuum of not less than 160 mm Hg. Two molar equivalents of an amine were added to the reaction flask, and the reaction mixture was brought to the reaction temperature. The reaction mixture then was maintained at the reaction temperature under an argon blanket for a sufficient time to complete the reaction. An alcohol was produced during the reaction, which was removed by distillation as the reaction proceeded. After the reaction was completed, a solid HAA was recrystallized from a methanol/ethyl acetate solution. Liquid HAAs typically were an oil which were heated at 50° C. under a high vacuum (<5 mm Hg) to remove residual starting materials.

Summary of Synthesis of HAAs

| Amine | g Amine | Ester | g Ester | g KOH[1] | Reaction Time (hr.) | Reaction Temp. (° C.) |
|---|---|---|---|---|---|---|
| ethanolamine | 28.050 | diethyl succinate | 40.000 | — | 72 | 100 |
| ethanolamine | 30.5000 | dimethyl glutarate | 40.000 | — | 17 | 100 |
| ethanolamine | 37.000 | dimethyl malonate | 40.000 | — | 2 | 20 |
| diethanolamine | 131.000 | dimethyl adipate | 106.000 | 0.500 | 5.75 | 100 |
| diethanolamine | 32.550 | dimethyl malonate | 20.000 | 0.145 | 4 | 100 |
| ethanolamine | 24.675 | dimethyl adipate | 20.000 | — | 17 | 100 |
| ethanolamine | 29.400 | diethyl oxalate | 20.000 | — | 17 | 20 |
| ethanolamine | 24.675 | diethyl maleate | 20.000 | — | 8 | 100 |

-continued

Summary of Synthesis of HAAs

| Amine | g Amine | Ester | g Ester | g KOH[1] | Reaction Time (hr.) | Reaction Temp. (° C.) |
|---|---|---|---|---|---|---|
| 2-(methylamino)ethanol | 22.875 | dimethyl malonate | 20.000 | — | 9 | 100 |
| 2-(methylamino)ethanol | 21.552 | diethyl succinate | 25.000 | 0.134 | 5 | 100 |
| 2-(methylamino)ethanol | 18.750 | dimethyl glutarate | 20.000 | 0.100 | — | 100 |
| diethanolamine | 28.767 | diethyl oxalate | 20.000 | — | 1.5 | 100 |
| 2-(methylamino)ethanol | 20.548 | diethyl oxalate | 20.000 | — | 1.5 | 100 |
| diethanolamine | 24.419 | diethyl maleate | 20.000 | — | 6.5 | 100 |
| 2-(methylamino)ethanol | 20.000 | diethyl maleate | 22.933 | — | 6.5 | 100 |
| diethanolamine | 24.138 | diethyl succinate | 20.000 | 0.110 | 6 | 100 |
| diethanolamine | 26.250 | dimethyl glutarate | 20.000 | 0.120 | 6 | 100 |
| diethanolamine | 26.923 | DBE-9[2] | 20.000 | 0.124 | 6 | 100 |
| ethanolamine | 15.640 | DBE-9[2] | 20.000 | 0.124 | 6.5 | 100 |
| 2-(methylamino)ethanol | 17.241 | dimethyl adipate | 20.000 | 0.110 | 6.5 | 100 |
| 2-(methylamino)ethanol | 19.231 | DBE-9 | 20.000 | 0.124 | 6.5 | 100 |
| ethanolamine | 15.062 | dimethyl diglycolate | 20.000 | 0.120 | 6.5 | 100 |
| diethanolamine | 25.926 | dimethyl diglycolate | 20.000 | 0.120 | 6.5 | 100 |
| 2-methylamino)ethanol | 18.206 | dimethyl diglycolate | 19.662 | 0.100 | 6.25 | 100 |

[1]grams of solid potassium hydroxide pellets (87% active); and
[2]DBE-9 is a commercial diester available from E. I. DuPont de Nemours, Wilmington, DE, and is a mixture of 66 wt % dimethyl succinate and 33 wt % dimethyl glutarate.

TABLE 3

| Sample | A[1] | L[1] | CR[2] | Temp.[3] | Time[4] | CRC[5] | 0.7 AUL |
|---|---|---|---|---|---|---|---|
| 14 | — | —C(O)NHCH$_2$CH$_2$OH | 0.01 | 165° C. | 180 min. | 30.0 | 21.8 |
| 15 | — | —C(O)N(CH$_3$)CH$_2$CH$_2$OH | 0.04 | 165° C. | 120 min. | 35.3 | 13.4 |
| 16 | — | —C(O)N(CH$_2$CH$_2$OH)$_2$ | 0.04 | 165° C. | 120 min. | 33.4 | 21.9 |
| 17 | —CH$_2$— | —C(O)NHCH$_2$CH$_2$OH | 0.12 | 165° C. | 120 min. | 29.6 | 22.4 |
| 18 | —CH$_2$— | —C(O)N(CH$_3$)CH$_2$CH$_2$OH | 0.10 | 165° C. | 120 min. | 29.8 | 22.6 |
| 19 | —CH$_2$— | —C(O)N(CH$_2$CH$_2$OH)$_2$ | 0.07 | 165° C. | 120 min. | 29.5 | 21.7 |
| 20 | —(CH$_2$)$_2$— | —C(O)NHCH$_2$CH$_2$OH | 0.05 | 165° C. | 180 min. | 31.4 | 24.3 |
| 21 | —(CH$_2$)$_2$— | —C(O)N(CH$_3$)CH$_2$CH$_2$OH | 0.07 | 165° C. | 120 min. | 29.8 | 24.5 |
| 22 | —(CH$_2$)$_2$— | —C(O)N(CH$_2$CH$_2$OH)$_2$ | 0.04 | 165° C. | 90 min. | 25.5 | 23.7 |
| 23 | —(CH$_2$)$_3$— | —C(O)NHCH$_2$CH$_2$OH | 0.07 | 165° C. | 180 min. | 30.0 | 24.4 |
| 24 | —(CH$_2$)$_3$— | —C(O)N(CH$_3$)CH$_2$CH$_2$OH | 0.04 | 165° C. | 90 min. | 26.7 | 25.2 |
| 25 | —(CH$_2$)$_3$— | —C(O)N(CH$_2$CH$_2$OH)$_2$ | 0.04 | 165° C. | 90 min. | 25.5 | 24.0 |
| 26 | —(CH$_2$)$_{2-3}$—[6] | —C(O)NHCH$_2$CH$_2$OH | 0.04 | 165° C. | 90 min. | 26.8 | 24.9 |
| 27 | —(CH$_2$)$_{2-3}$—[6] | —C(O)N(CH$_3$)CH$_2$CH$_2$OH | 0.04 | 165° C. | 90 min. | 26.8 | 24.9 |
| 28 | —(CH$_2$)$_{2-3}$—[6] | —C(O)N(CH$_2$CH$_2$OH)$_2$ | 0.04 | 165° C. | 90 min. | 25.1 | 24.0 |
| 29 | —(CH$_2$)$_4$— | —C(O)NHCH$_2$CH$_2$OH | 0.10 | 165° C. | 120 min. | 28.6 | 23.7 |
| 30 | —(CH$_2$)$_4$ | —C(O)N(CH$_3$)CH$_2$CH$_2$OH | 0.04 | 165° C. | 120 min. | 33.4 | 20.8 |
| 31 | —(CH$_2$)$_4$— | —C(O)N(CH$_2$CH$_2$OH)$_2$ | 0.04 | 165° C. | 120 min. | 29.6 | 22.0 |
| 32 | —CH=CH— | —C(O)NHCH$_2$CH$_2$OH | 0.04 | 165° C. | 120 min. | 33.2 | 11.9 |
| 33 | —CH=CH— | —C(O)N(CH$_3$)CH$_2$CH$_2$OH | 0.04 | 165° C. | 120 min. | 35.7 | 12.5 |
| 34 | —CH=CH— | —C(O)N(CH$_2$CH$_2$OH)$_2$ | 0.04 | 165° C. | 120 min. | 34.5 | 17.8 |
| 35 | —CH$_2$OCH$_2$— | —C(O)NHCH$_2$CH$_2$OH | 0.04 | 165° C. | 60 min. | 29.2 | 18.5 |
| 36 | —CH$_2$OCH$_2$— | —C(O)N(CH$_3$)CH$_2$CH$_2$OH | 0.04 | 165° C. | 60 min. | 28.8 | 19.9 |
| 37 | —CH$_2$OCH$_2$— | —C(O)N(CH$_2$CH$_2$OH)$_2$ | 0.04 | 165° C. | 60 min. | 28.2 | 21.3 |
| 38 | —(CH$_2$)$_{2-3-4}$—[7] | —C(O)N(CH$_2$CH$_2$OH)$_2$ | 0.04 | 165° C. | 90 min. | 24.9 | 23.7 |
| 39 | —(CH$_2$)$_{3-4}$—[8] | —C(O)N(CH$_2$CH$_2$OH)$_2$ | 0.04 | 165° C. | 90 min. | 25.9 | 23.6 |
| Comparative 40 | Ethylene glycol diglycidyl ether | | 0.04 | 165° C. | 60 min. | 30.5 | 24.0 |

[1]Component of the surface crosslinking compound of the formula L-A-L;
[2]CR is a weight ratio of surface crosslinking compound applied to the surface of the SAP particles, based on SAP weight;
[3]Heating temperature;
[4]Curing time;
[5]CRC is retention capacity, in g 0.9% NaCl per g of dry SAP, the CRC of control SAP particles lacking surface crosslinks is 34.3;
[6]blend of 33% —(CH$_2$)$_2$— and 67% —(CH$_2$)$_3$—;
[7]blend of 20% —(CH$_2$)$_2$, 60% —(CH$_2$)$_3$, and 20% —(CH$_2$)$_4$—; and
[8]blend of 75% —(CH$_2$)$_3$ and 25% —(CH$_2$)$_4$—.

The data in Table 3 shows that surface crosslinking using an HAA provides surface-treated SAP particles having a comparable AUL (Samples 14–39) compared to SAP particles surface crosslinked with a diglycidyl ether (Comparative Sample 40). In addition, an HAA surface crosslinker did not adversely affect the CRC.

Preferred SAP particles of the present invention are surface crosslinked with an HAA, and have a 0.7 AUL of at least 15, and more preferably at least 20. The preferred surface crosslinked SAP particles typically have a 0.7 AUL of about 15 to about 50. Preferred SAP particles of the present invention also have a CRC of less than 32.4, and more preferably less than 31.5. Preferred SAP particles typically have a CRC of less than 32.4 to about 25. The properties exhibited by the HAA surface-crosslinked SAP particles illustrate that HAA can be substituted for currently used surface-crosslinking agents, like EGDGE, and overcome disadvantages associated with such crosslinking agents, e.g., color degradation.

The surface crosslinked SAP particles of the present invention can be used as an absorbent in disposable diapers, sanitary napkins, and similar articles, and can be used in other applications, for example, a dew formation inhibitor for building materials, a water-holding agent for agriculture and horticulture, and a drying agent.

Surface-crosslinked SAP particles of the present invention have advantages over conventional absorbent particles. The surface-crosslinked SAP particles of the invention can be produced at a low cost by a simple method which involves mixing SAP particles with the HAA and heating. The resulting surface-crosslinked SAP particles are less susceptible to fish eye formation than conventional absorbent resins and, therefore, exhibit a high rate of liquid absorption The present surface-crosslinked SAP particles also are white to off-white in color.

Obviously, many modifications and variations of the invention as hereinbefore set forth can be made without departing from the spirit and scope thereof, and, therefore, only such limitations should be imposed as are indicated by the appended claims.

What is claimed is:

1. Superabsorbent polymer particles comprising 100 parts by weight of a water-absorbing resin and about 0.001 to about 10 parts by weight of a hydroxyalkylamide, wherein the hydroxyalkylamide is present at surfaces of the water-absorbing resin and crosslinks polymer chains at the surfaces of the water-absorbing resin.

2. The particles of claim 1 wherein the particles contain about 0.01 to about 4 parts by weight of the hydroxyalkylamide, per 100 parts by weight of the water-absorbing resin.

3. The particles of claim 1 wherein the particles contain about 0.4 to about 2 parts by weight of the hydroxyalkylamide, per 100 parts by weight of the water-absorbing resin.

4. The particles of claim 1 wherein the hydroxyalkylamide has the structure

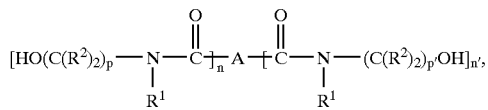

wherein A is a bond, hydrogen, a monovalent or polyvalent organic radical selected from the group consisting of a saturated or unsaturated alkyl radical containing 1 to 60 carbon atoms, aryl, tri-$C_{1-4}$ alkyleneamine, and an unsaturated radical containing one or more ethylenic groups; $R^1$, selected independently, are hydrogen, straight or branched chain $C_{1-5}$ alkyl, or straight or branched chain $C_{1-5}$ hydroxyalkyl; $R^2$, selected independently, are radicals selected from the group consisting of hydrogen and straight or branched $C_{1-5}$ alkyl, or the $R^2$ radicals are joined to form, together with carbon atoms, a cycloalkyl ring; p and p', independently, are an integer 1 to 4; n is an integer having a value of 1 or 2, and n' is an integer having a value of 0 to 2; or when n' is 0, a polymer or copolymer, wherein n is greater than 1 formed from the hydroxyalkylamide when A is an unsaturated radical.

5. The particles of claim 4 wherein the hydroxyalkylamide has the structure

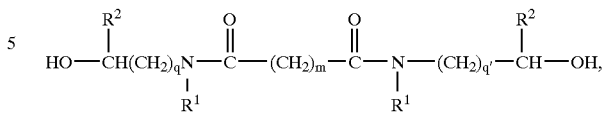

wherein $R^1$ is H or $C_{1-5}$ hydroxyalkyl, m is 0–8, and one of the $R^2$ radicals on the beta carbon is H and the other is H or a $C_{1-5}$ alkyl, and q and q', independently, are an integer 1 to 3.

6. The particles of claim 4 wherein the hydroxyalkylamide has the structure

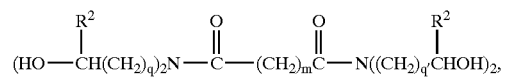

wherein both $R^2$ groups are H or both $R^2$ groups are —$CH_3$.

7. The particles of claim 1 wherein the hydroxyalkylamide has the structure

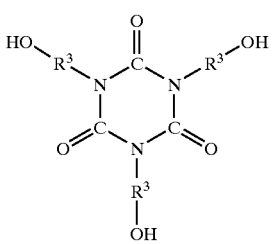

where $R^3$ is a divalent radical selected from the group consisting of an alkylene radical containing 1 to 4 carbon atoms and arylene.

8. The particles of claim 1 wherein the hydroxyalkylamide is selected from the group consisting of bis[N,N-di(β-hydroxyethyl)]adipamide, bis[N,N-di(β-hydroxypropyl)]succinamide, bis[N,N-di(β-hydroxyethyl)]azelamide, bis[N-N-di(β-hydroxypropyl)]adipamide, bis[N-methyl-N-(β-hydroxyethyl)]oxamide, and mixtures thereof.

9. The particles of claim 1 wherein the hydroxyalkylamide has the structure

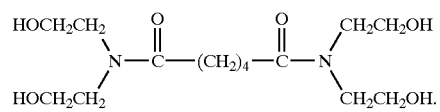

10. The particles of claim 1 wherein the hydroxyalkylamide has the structure

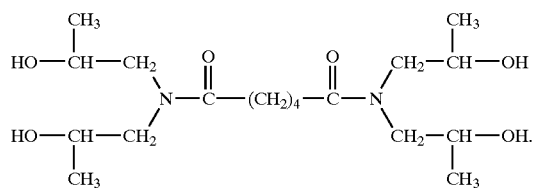

11. The particles of claim 1 the hydroxyalkylamide has a structure L—A—L, wherein A is selected from the group consisting of $(CH_2)_n$, $CH=CH$, and $CH_2OCH_2$, L, independently, is selected from the group consisting of —C(=O)N(CH$_3$)CH$_2$CH$_2$OH, —C(=O)NHCH$_2$CH$_2$OH, and —C(=O)N(CH$_2$CH$_2$OH)$_2$, and n is 0, 1, 2, 3, or 4.

12. The particles of claim 11 wherein the hydroxyalkylamide is selected from the group consisting of bis[N-methyl-N-(β-hydroxyethyl)]succinamide, bis[N-methyl-N-(β-hydroxyethyl)]glutaramide, bis[N-methyl-N-(β-hydroxyethyl)]succinamide/glutaramide, bis[N,N-(dihydroxyethyl)]succinamide, bis[N,N-(dihydroxyethyl)]glutaramide, bis[N,N-(dihydroxyethyl)]succinamide/glutaramide, bis[N,N-(dihydroxyethyl)]succinamide/glutaramide/adipamide, bis[N,N-(dihydroxyethyl)]glutaramide/adipamide, and mixtures thereof.

13. The particles of claim 11 wherein the hydroxyalkylamide comprises a reaction product of a reaction between (a) ethanolamine, diethanolamine, 2-(methylamino)ethanol, and mixtures thereof, and (b) a diethyl or a dimethyl ester of succinic acid, glutaric acid, malenic acid, oxalic acid, adipic acid, maleic acid, and mixtures thereof.

14. The particles of claim 1 wherein the water-absorbing resin comprises an acidic water-absorbing resin.

15. The particles of claim 14 wherein the acidic water-absorbing resin is a neutralized, lightly crosslinked acrylic-type resin containing at least 10% acidic monomer units.

16. The particles of claim 15 wherein the acidic monomer units have a carboxylate, sulfonate, sulfate, or phosphate group.

17. The particles of claim 14 wherein the acidic monomer units are selected from the group consisting of acidic water-absorbing resin include acrylic acid, methacrylic acid, ethacrylic acid, α-chloroacrylic acid, α-cyanoacrylic acid, β-methylacrylic acid, α-phenylacrylic acid, β-acryloxypropionic acid, sorbic acid, α-chlorosorbic acid, angelic acid, cinnamic acid, p-chlorocinnamic acid, β-stearylacrylic acid, itaconic acid, citraconic acid, mesaconic acid, glutaconic acid, aconitic acid, maleic acid, fumaric acid, tricarboxyethylene, 2-methyl-2-butene dicarboxylic acid, maleamic acid, N-phenyl maleamide, maleamide, maleic anhydride, fumaric anhydride, itaconic anhydride, citraconic anhydride, mesaconic anhydride, methyl itaconic anhydride, ethyl maleic anhydride, diethylmaleate, methylmaleate, maleic anhydride, vinylsulfonic acid, allyl sulfonic acid, vinyl toluene sulfonic acid, styrene sulfonic acid, an acrylic sulfonic acid, a methacrylic sulfonic acid, sulfoethyl acrylate, sulfoethyl methacrylate, sulfopropyl acrylate, 2-vinyl-4-ethylbenzene, 2-allylbenzene sulfonic acid, 1-phenylethylene sulfonic acid, sulfopropyl methacrylate, 2-hydroxy-3-methacryloxypropyl sulfonic acid, 2-acrylamide-2-methylpropane sulfonic acid, sulfated polyvinylalcohol, sulfated hydroxyethyl acrylate, sulfated hydroxypropyl methacrylate, methacryloxyethyl phosphate, and mixtures thereof.

18. The particles of claim 14 wherein the acidic water-absorbing resin is selected from the group consisting of a starch-acrylic acid graft copolymers, a saponified vinyl acetate-acrylic ester copolymer, a hydrolyzed acrylonitrile copolymer, a hydrolyzed acrylamide copolymer, an ethylene-maleic anhydride copolymer, an isobutylene-maleic anhydride copolymer, poly(vinylsulfonic acid), poly(vinylphosphonic acid), poly(vinylphosphoric acid), poly(vinylsulfuric acid), sulfonated polystyrene, poly(aspartic acid), poly(lactic acid), and mixtures thereof, neutralized 20 to 100 mole percent with a base.

19. The particles of claim 1 wherein the water-absorbing resin is polyacrylic acid neutralized 50 to 100 mole percent.

20. The particles of claim 1 wherein the water-absorbing resin comprises a basic water-absorbing resin.

21. The particles of claim 20 wherein the basic water-absorbing resin is a neutralized, lightly crosslinked resin containing at least 10% basic monomer units.

22. The particles of claim 20 wherein the basic water-absorbing resin is selected from the group consisting of a poly(vinylamine), a poly(alkylaminoalkyl (meth)acrylamide, a polyethylenimine, a poly(allylamine), a poly(allylguanidine), a poly(dimethylallylammonium hydroxide), a quaternized polystyrene, a guanidine-modified polystyrene, a quaternized poly(meth)acrylamide or ester analog thereof, a poly(vinylguanidine), and mixtures thereof.

23. The particles of claim 1 wherein the water-absorbing resin comprises a mixture of an acidic water-absorbing resin and a basic water-absorbing resin.

24. The particles of claim 1 wherein the water-absorbing resin comprises multicomponent superabsorbent polymer particles.

25. The particles of claim 1 having an absorption under a load of 0.7 psi after one hour of at least 20 grams of 0.9% saline per gram of particles.

26. The particles of claim 1 having an AUL at 0.7 psi of greater than 15 and a CRC of less than 32.4.

27. The particles of claim 1 having an AUL at 0.7 psi or greater than 20.

28. The particles of claim 27 having a CRC of less than 31.5.

29. Surface crosslinked superabsorbent polymer particles obtained by mixing 100 parts, by weight, of a superabsorbent polymer with about 0.001 to about 10 parts, by weight, of a hydroxyalkylamide to form surface-treated superabsorbent polymer particles, then heating the surface-treated superabsorbent particles at about 90° C. to about 170° C. for about 60 to about 180 minutes to form surface crosslinks on the surface-treated superabsorbent polymer particles.

30. A method of preparing surface crosslinked superabsorbent polymer particles comprising:
  (a) providing 100 parts by weight of superabsorbent polymer particles;
  (b) forming a solution comprising about 0.5% to about 50% by weight of a hydroxyalkylamide in a solvent capable of solubilizing the hydroxyalkylamide;
  (c) applying the solution of (b) to surfaces of (a) to provide surface-treated superabsorbent polymer particles having about 0.001 to about 10 parts, by weight, of the hydroxyalkylamide per 100 parts, by weight, of superabsorbent polymer particles in the vicinity of the surfaces of the superabsorbent polymer particles; and
  (d) heating the surface-treated superabsorbent polymer particles at about 90° C. to about 170° C. for about 60 to about 180 minutes to form surface crosslinks in the vicinity of the surface of the superabsorbent polymer particles.

31. The method of claim 30 wherein step (c) is performed prior to step (d).

32. The method of claim 30 wherein steps (c) and (d) are performed simultaneously.

33. The method of claim 30 wherein the hydroxyalkylamide solution of step (b) further comprises a second surface crosslinking agent selected from the group consisting of a diol, a triol, a polyol, a divalent metal, a trivalent metal, a diglycidyl ether, a diamine, a halohydrin, a polyisocyanate, a dihaloalkane, a polyfunctional aziridine compound, a dialdehyde, a disulfonate ester, a diester, a multifunctional acid halide, an organic titanate, a melamine resin, a hydroxymethyl urea, and mixtures thereof.

34. The method of claim 33 wherein the second surface crosslinking agent comprises ethylene glycol, propylene glycol, 1,3-butanediol, 1,4-butanediol, ethylene glycol diglycidyl ether, and mixtures thereof.

35. The method of claim 30 wherein the hydroxyalkylamide solution of step (b) further comprises a second surface crosslinking agent capable of forming surface crosslinks on the superabsorbent polymer particles at a temperature of about 90° C. to about 160° C.

36. A method of preparing surface crosslinked superabsorbent polymer particles comprising:

(a) polymerizing a mixture containing (i) unsaturated polymerizable monomers having acid groups or basic groups, and (ii) a polyfunctional crosslinking agent, dissolved in (iii) a solvent comprising water to form a superabsorbent polymer hydrogel;

(b) adding a sufficient amount of a hydroxyalkylamide to the superabsorbent polymer hydrogel to provide about 0.001 to about 10 parts, by weight, of the β-hydroxyalkylamide per 100 parts, by weight, of the superabsorbent polymer; and (c) heating the product of step (b) at about 90° C. to about 170° C. to dry the superabsorbent polymer hydrogel, form superabsorbent polymer particles, and form crosslinks on the surface of the superabsorbent polymer particles.

37. Surface crosslinked superabsorbent polymers prepared by the method of claim 36.

38. An article comprising the superabsorbent particles of claim 1.

39. The article of claim 38 wherein the article is a diaper or a catamenial device.

* * * * *